United States Patent [19]

Mosimann

[11] Patent Number: 4,773,856
[45] Date of Patent: Sep. 27, 1988

[54] DEVICE FOR ACTUATING A TOOL FASTENING AND RELEASING MECHANISM

[76] Inventor: David Mosimann, 13-15 chemin des Grillons, CH-2500 Bienne 6, Switzerland

[21] Appl. No.: 51,870

[22] Filed: May 19, 1987

[30] Foreign Application Priority Data

May 13, 1986 [CH] Switzerland .......................... 1937/86

[51] Int. Cl.[4] ............................................... A61C 1/14
[52] U.S. Cl. ..................................... 433/127; 433/129
[58] Field of Search ................................. 433/127, 129

[56] References Cited

U.S. PATENT DOCUMENTS 2,895,738  7/1959  Baker ..................................... 433/129
3,082,528  3/1963  Reid ...................................... 433/127

FOREIGN PATENT DOCUMENTS 2905484  8/1979  Fed. Rep. of Germany ...... 433/127

Primary Examiner—John J. Wilson
Attorney, Agent, or Firm—McGlew and Tuttle

[57] ABSTRACT

A device for releasing a tool from a tool fastening mechanism of a dentist's handpiece comprises a push-piece that is held in an outer, inoperative position by a spring, and a slide mounted on a rotor of the dentist's handpiece. Upon being pressed, the push-piece engages the slide to release a tool fastened in the rotor. In order to prevent the push-piece from overheating when it is in contact with the slide while the slide is rotating at high speed, the push-piece carries a disc and the slide carries a ball. The disc and the ball are for instance made of sintered hard metal and are located where the push-piece and the slide engage such as to have substantially a point contact between them on the rotational axis of the slide.

3 Claims, 1 Drawing Sheet

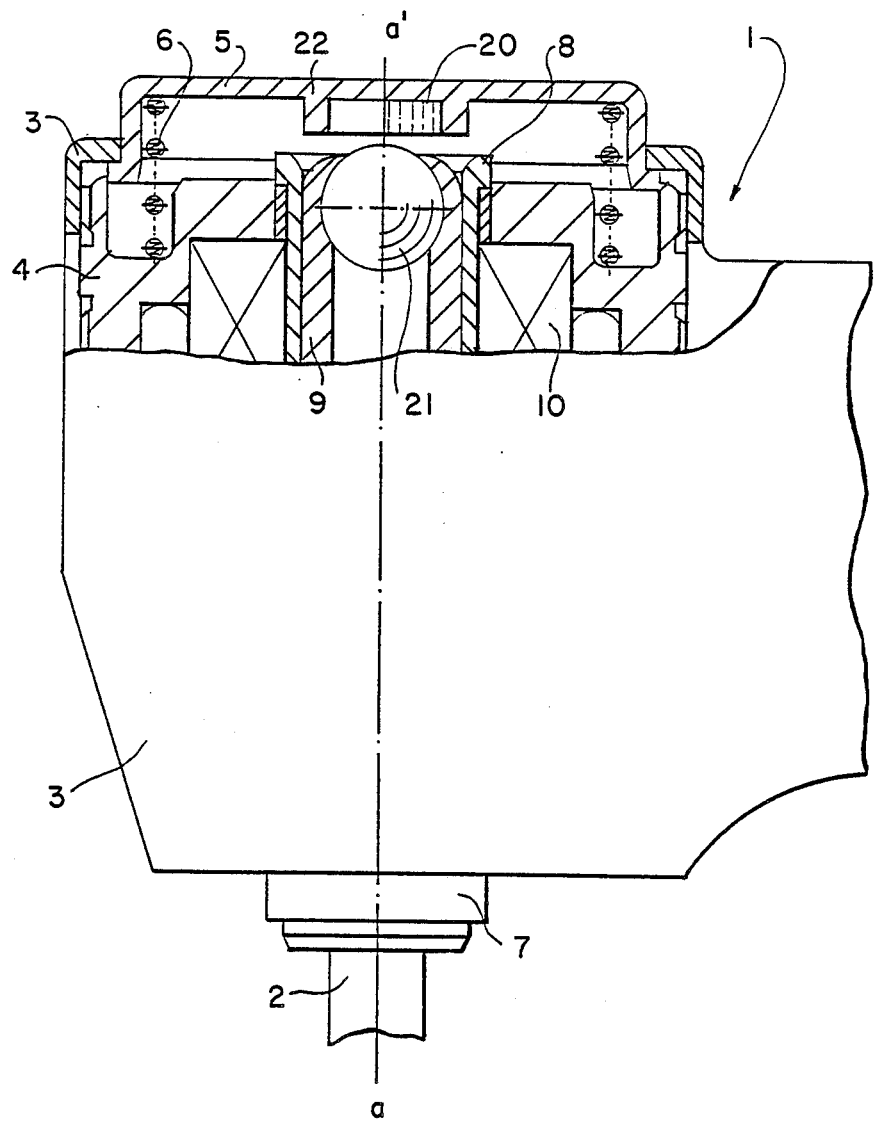

DEVICE FOR ACTUATING A TOOL FASTENING AND RELEASING MECHANISM

FIELD AND BACKGROUND OF THE INVENTION

The present invention relates in general to manually actuatable devices used to fasten a tool such as the rotor of a dentist's handpiece, and in particular to a new and useful device which comprises a push-piece and a rotary shaft, wherein the push-piece engages the shaft in response to an actuating force in order to act on tool fastening means to release a tool.

Such actuating devices are well-known. For instance, a device of this kind is used in the dentist's handpiece that is disclosed in U.S. Pat. No. 4,012,841 (which is incorporated here by reference). In this arrangement, a push-piece that is held in an outer, inoperative position by a spring, engages a rotary shaft in response to an inwardly acting force. This shaft in turn cooperates with a fastening spring provided inside a cylindrical body and the resulting unit, which forms the rotor of the handpiece, is rotatably driven at high speed by a motor. The force exerted on the push-piece is transmitted to the fixing spring to compress it. Such compression causes the inner diameter of the spring to increase thereby enabling the shank of a tool, such as that of a drilling tool, to be inserted into the spring. On releasing the force on the spring, the tool becomes fastened in the rotor. The portions of the push-piece and of the shaft that are made to engage one another are flat in the above arrangement. This produces a substantial area of contact and a high coefficient of friction between the push-piece and the shaft when they come into contact. This basically is unimportant since the push-piece only acts on the shaft when the drilling tool is being changed, while the rotor is at rest. Also, to decrease the force having to be exerted on the push-piece and hence facilitate tool changes, use is made of a soft springe to hold the push-piece in its outer, inoperative position.

A soft spring however is the cause of some drawbacks; when a dentist uses the handpiece the push-piece may inadvertently come into contact with some part of the buccal cavity. If the pressure due to this contact is such that the push-piece compresses the spring and engages the shaft which is then rotating at a speed (which may be in excess of 100,000 rpm) it will rapidly overheat because of the high coefficient of friction that exists between these two parts. Such overheating may cause a local burn on the patient and may lead to sudden and uncontrolled movements of the part of the patient. If the affected part is anaesthetized, the burn could be worse as the patient will not feel it and will have no warning reaction that will cause the dentist to move his instrument.

SUMMARY OF THE INVENTION

An object of the present invention is to overcome the drawbacks mentioned above by providing an actuating device involving two parts that are movable in relation to one another and that are meant to come into contact with each other, wherein the temperature of these two parts, upon coming into contact, will be prevented from rising excessively.

The device according to the invention comprises a push-piece that is movable along an axis and a shaft that is rotatable about said axis, said push-piece and said shaft having portions arranged to engage one another whereby an actuating force applied to said push-piece may be transmitted to said shaft, said portions defining between them substantially point contact centered on said axis to reduce the coefficient of friction between said push-piece and said shaft.

A further object of the present invention is to provide a device for releasing a tool from a shaft which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

The single FIGURE of the accompanying drawing is a side view, partly in axial section, of one end portion of a dentist's handpiece fitted with an actuating device according to the inventon.

DESCRIPTION OF THE PREFERRED EMBODIMENT

In the drawing a handpiece 1 comprises a head which is inserted into the buccal cavity of a patient's mouth to treat a tooth (not shown) using a tool 2, e.g. a drilling tool, of which only the shank is visible.

The stationary portion of the head comprises a housing 3 in which is secured a ring 4. A push-button 5 projecting out of housing 3 is mounted above ring 4. A coil spring 6 is provided between ring 4 and push-button 5 to hold the push-button 5 in an outer, inoperative position. By applying a downward force on push-button 5, spring 6 is compressed and push-button 5 is pressed inwardly along an axis aa' about which push-button 5 is not free to rotate.

A rotor 7 is mounted inside housing 3 and a tool 2 is fastened to the rotor 7. Rotor 7 comprises ahollow shaft 8, into which is inserted the shank of tool 2, and a tubular slide 9. Shaft 8 is supported in ball bearings 10 which enable it to rotate about axis aa' while preventing it from moving axially. Slide 9, which lies inside shaft 8, is arranged to rotate with the shaft, but is free to move axially thereof. Rotor 7 also comprises a fastening device that cooperates with slide 9 and which enables the shank of tool 2 to be held therein by clamping members. Further, a motor (not shown), e.g. an air turbine, that is fixed to shaft 8, is provided in the housing or head to drive the rotor at speeds of 500,000 rpm or more. Details of the fastening means for fastening the shank of tool 2 to the shaft 8, are found for example in the above-identified U.S. Pat. No. 4,012,841, so that further details of this structure are not given here. Any other known fastening mechanism can also be used as long as it acts to connect and disconnect the tool 2 by axial movement of the slide 9.

To release the shank of tool 2 an axial force sufficient to act on the clamping members of the fastening device must be applied onto slide 9. This is done by pressing push-button 5 so that it engages slide 9, which projects slightly from shaft 8 for this purpose. The pressure exerted on push-button 5 thus enables tool 2 to be released from rotor 7 whereby it may, for instance, be replaced by another tool.

In known constructions, the inner surface of push-button 5 and the end portion of slide 9 lying opposite this surface are substantially flat and parallel. These two parts thus engage one another over a substantial area of contact, thereby giving rise to a large frictional coefficient between them.

In normal use this is unimportant since the rotor is then stationary, as pointed out earlier. Accidental engagement of the two parts, however, while the rotor revolves at high speed firstly causes rapid wear of the contacting surfaces and secondly, and more importantly, causes overheating of the push-button with temperatures easily in excess of 100° C., thereby causing pain to the mucosae of the patient should the push-button come into contact with them.

To avoid these difficulties in the illustrated arrangement, a disc 20 is provided on the inside of push-button 5 and a ball 21, centered on axis aa', is provided at the tip end of slide 9 in facing relationship with disc 20. Disc 20 is mounted in a recessed boss 22 on the inside of push-button 5, as by bonding, while ball 21 is held in slide 9 by crimping.

The mutually engageable portions of push-button 5 and of slide 9 consist, in the illustrated embodiment, of a flat surface and of a spherical surface that define between them a substantial point contact. To ensure such point contact, even when a large force is applied on push-button 5, disc 20 and ball 21 are preferably made of sintered hard metal. And with ball 21 being centered on axis aa' the above point contact will be suitably centered.

Because of the extremely reduced area of contact and because this area is centered on axis aa', which is also the rotational axis of slide 9, the coefficient of friction between push-button 20 and rotor 7 is very much reduced. Since a low coefficient of friction means reduced heating and hence only a slight increase in temperature of the contacting portions, the main object of the invention is satisfied.

The surfaces that define the contacting portions may have shapes other than those described and illustrated, but at least one of the surfaces is preferably a surface of revolution with axis aa' as its axis of symmetry.

Preferably both portions are made of a hard material such as sintered hard metal, sapphire, tempered steel or ceramic. A different material may be used for each portion.

The engageable portions may either form part of separate elements mounted on the push-button or the slide or form an integral part of the push-button and of the slide.

While a specific embodiment of the invention has been shown and described in detail to illustrate the application of the principles of the invention, it will be understoood that the invention may be embodied otherwise without departing from such principles.

What is claimed is:

1. A device for releasing a tool held by fastening means, comprising a shaft mounted for rotation about an axis having at least one portion which is also movable axially with respect to said axis for releasing the tool, a push-piece mounted for axial movement at a location spaced from said shaft and movable axially toward said shaft, said push-piece having a portion engageable with said portion of said shaft for moving said portion of said shaft axially to release the tool, said portions of said push-piece and shaft being shaped to form a point contact therebetween when said push-piece is moved axially toward said shaft, said point contact being centered on said axis of rotation, one of said portions of said push-piece defining a surface of revolution around said point contact which is axially symmetrical to said axis of rotation, the other of said portions of said push-piece and said shaft being flat around said point contact and extending transversely to said axis of rotation, said portion of shaft includes a slide and a hollow shaft portion, said slide being mounted for axial sliding in said hollow shaft poriton, a ball connected to said slide and having a portion extending outwardly of said slide toward said push-piece, said portion of said push-piece comprising a flat disc facing said ball.

2. A device according to claim 1 wherein said portions of said push-piece and said shaft are each made of material which is harder than remaining portions of said push-piece and said shaft.

3. A device according to claim 1 including a housing, said hollow shaft being mounted for rotation about said axis in said housing, a ring mounted in said housing for supporting said hollow shaft, said push-piece being mounted for axial movement to said housing, and a spring engaged between said push-piece and said ring for urging said push-piece out of said housing in away from said slide.

* * * * *